United States Patent [19]

Vetter et al.

[11] Patent Number: 5,069,670

[45] Date of Patent: Dec. 3, 1991

[54] HYPODERMIC SYRINGE

[75] Inventors: Helmut Vetter, Ravensburg; Peter Geprägs, Weingarten, both of Fed. Rep. of Germany

[73] Assignee: Arzneimittel GmbH Apotheker Vetter & Co., Ravensburg, Fed. Rep. of Germany

[21] Appl. No.: 578,731

[22] Filed: Sep. 6, 1990

[51] Int. Cl.$^5$ ............................................. A61M 5/00
[52] U.S. Cl. ................................. 604/243; 604/82; 604/218
[58] Field of Search ............... 604/243, 187, 110, 111, 604/82, 240, 228, 86, 88, 218

[56] References Cited

U.S. PATENT DOCUMENTS

| | | | |
|---|---|---|---|
| 2,661,740 | 12/1953 | Hickey | 604/228 |
| 4,129,130 | 12/1978 | Bigarella | 604/243 X |
| 4,185,628 | 1/1980 | Kopfer | 604/82 |
| 4,226,236 | 10/1980 | Genese | 604/89 |
| 4,240,425 | 12/1980 | Akhavi | 604/243 |
| 4,781,701 | 11/1988 | Geprags | 604/240 |

Primary Examiner—John D. Yasko
Attorney, Agent, or Firm—Herbert Dubno; Andrew Wilford

[57] ABSTRACT

A hypodermic syringe has a generally cylindrically tubular body extending along an axis and having an axial front end formed with a radially outwardly projecting annular bead, a piston axially displaceable in the body, a plug having a rearwardly directed flange fitting complementarily over the front end of the body at the bead and forwardly blocking the body, and a flat soft seal ring compressed axially between the plug and the front end of the body. The body has a rear end provided with a finger-rest crosspiece and the piston is provided with a plunger projecting axially out the rear end past the crosspiece.

8 Claims, 3 Drawing Sheets

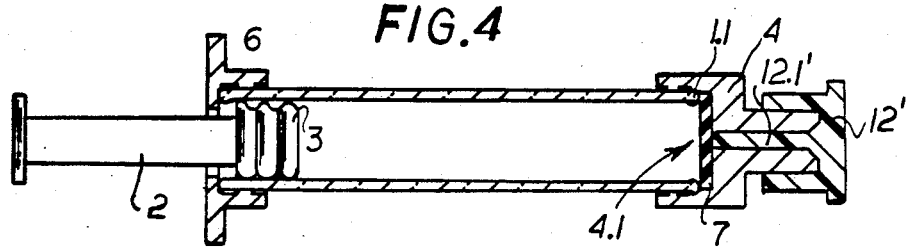
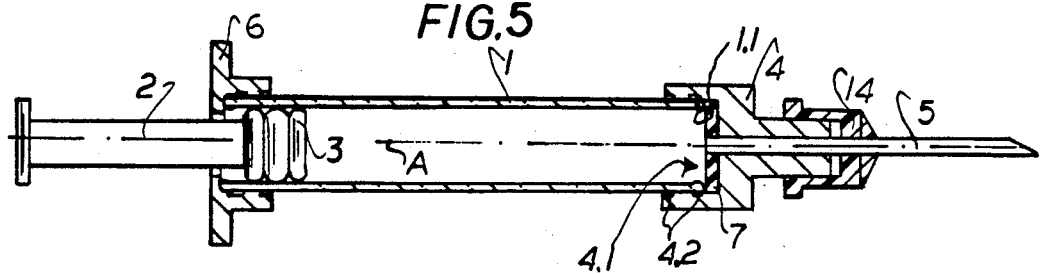
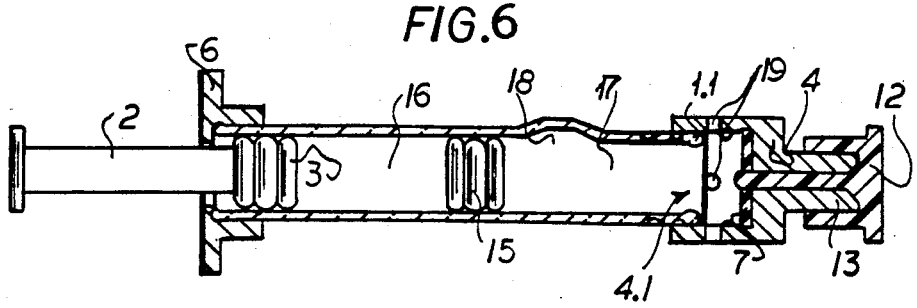

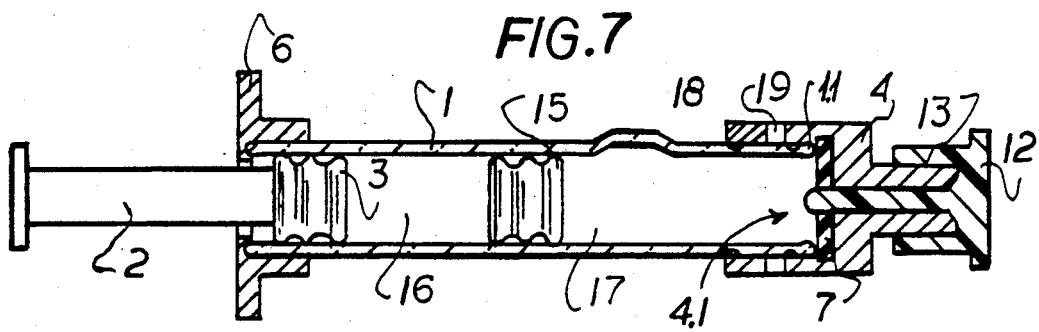
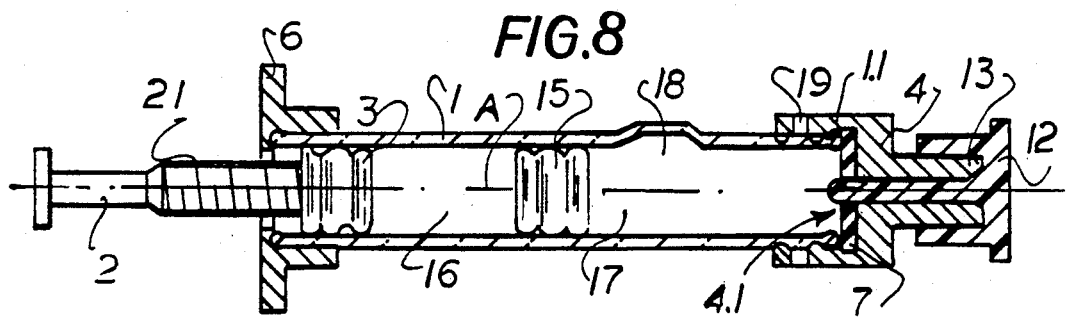
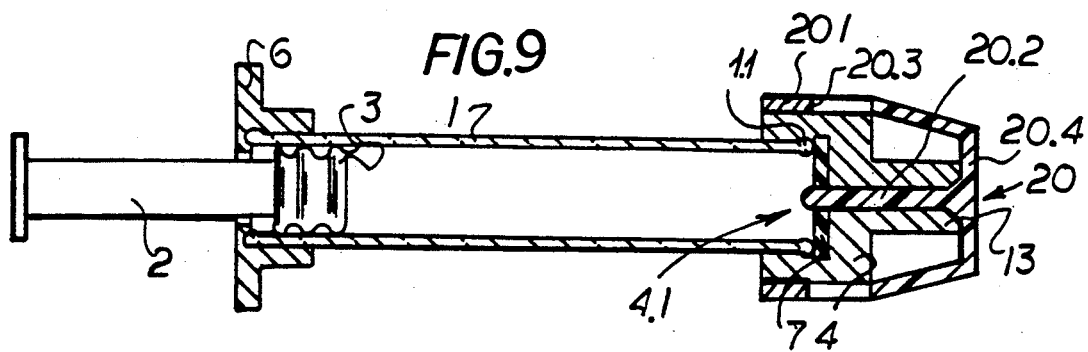

5,069,670

HYPODERMIC SYRINGE

FIELD OF THE INVENTION

The present invention relates to a hypodermic syringe. More particularly this invention concerns such a syringe of the throwaway single-use type.

BACKGROUND OF THE INVENTION

A standard hypodermic syringe has a cylindrical body having a front end fitted with a cap in turn carrying a needle that projects along the axis of the body into the body and a rear end sealed by a piston carried on a plunger. The plunger is pressed forward to pressurize a liquid in the body and force it forward out of the body through the needle.

To meet current hygienic standards it is nowadays standard to make such a hypodermic assembly as a throwaway item intended for only a single use. Thus it must be made at the lowest possible cost. At the same time the hypodermic must be certain to work perfectly, and must be protected against or at least provide a visual indication of tampering or an unhygienic condition.

OBJECTS OF THE INVENTION

It is therefore an object of the present invention to provide an improved hypodermic syringe.

Another object is the provision of such an improved hypodermic syringe which overcomes the above-given disadvantages, that is which is extremely cheap to manufacture while still being of high quality.

SUMMARY OF THE INVENTION

A hypodermic syringe according to the invention has a generally cylindrically tubular body extending along an axis and having an axial front end formed with a radially outwardly projecting annular bead, a piston axially displaceable in the body, a plug having a rearwardly directed flange fitting complementarily over the front end of the body at the bead and forwardly blocking the body, and a flat soft seal ring compressed axially between the plug and the front end of the body. The body has a rear end provided with a finger-rest crosspiece and the piston is provided with a plunger projecting axially out the rear end past the crosspiece.

It is therefore possible to make the syringe body out of a piece cut off a length of glass tubing, for instance. Heating the ends of the cut piece simultaneously eliminates sharp edges while making beads suitable for anchoring both the front plug and the rear crosspiece.

According to this invention a needle is secured adhesively into the plug and has a rear end and a front end. The seal ring is formed with a central opening fitting around the rear needle end and the plug is formed with a radially outwardly projected securing rim. A needle protector is fitted over the needle and snugly engages around the rim. This needle protector can be made of a hard plastic and is provided with a soft seal body into which a front end of the needle is poked. Thus the entire assembly, even filled if desired, can be provided as a prepackaged unit with the needle tip protected.

A tip cap fitted over the plug can be formed with a rearwardly projecting pin extending axially through the plug. The seal ring is formed with a central opening fitting snugly around the pin of the tip cap or the pin has a rear end slightly axially forward of the seal ring. In the latter case the needle is used to pierce the seal ring. The plug according to this invention can also have a forwardly projecting collar adapted to fit with a separate needle assembly and is made of a hard elastomer.

For a so-called mixing syringe a partition plug is axially slidable in the body between the piston and the front body end and forms in the body a rear compartment adapted to hold a solvent and a front compartment adapted to hold a dissolvable medicament. The body is formed generally centrally with an inwardly open bypass groove and the flange of the plug is formed with at least one radially throughgoing orifice. The plug is displaceable between a front position with the orifice forward of the body front end and thereby venting the front compartment and a rear position with the orifice backward of the body front end and blocked by the body. When in the front position it is possible to lyophilize a liquid medicament held in the front compartment, and then to simply seal the resultant dried mass in the front compartment by pushing the plug into its rear position.

It is also possible according to this invention for the body to have a rear end provided with a finger-rest crosspiece and for the piston to be provided with a plunger projecting axially out the rear end past the crosspiece. This crosspiece is internally threaded and the plunger has an externally threaded front portion complementarily engaged in the crosspiece and a small-diameter rear portion slidable axially through the crosspiece.

A protective cap according to this invention is made of a hard but frangible material covering the plug and is formed with a rear end fixed permanently to the plug, a front end fitting over and covering the plug, a pin projecting axially backward from the front end through the plug, and a weakened region joining the protective-cap front and rear ends.

DESCRIPTION OF THE DRAWING

The above and other objects, features, and advantages will become more readily apparent from the following, it being understood that any feature described with reference to one embodiment of the invention can be used where possible with any other embodiment and that reference numerals or letters not specifically mentioned with reference to one figure but identical to those of another refer to structure that is functionally if not structurally identical. In the accompanying drawing:

FIGS. 2, 3, 4, and 5 are views like FIG. 1 of variants on the system of FIG. 1;

FIG. 6 is an axial section through another syringe assembly in accordance with this invention;

FIG. 7 is another axial section through the syringe of FIG. 6 in another position;

FIG. 8 is a view like FIG. 6 of a variant on the system of FIG. 6; and

FIG. 9 is an axial section through another variant on the system of FIG. 1.

SPECIFIC DESCRIPTION

Figure 1:
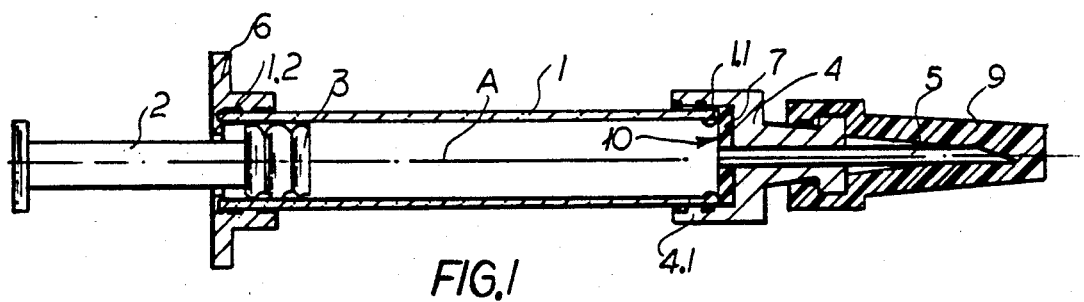
FIG. 1 is an axial section through a hypodermic syringe assembly according to the invention.

As seen in FIG. 1 a hypodermic syringe according to this invention has a tubularly cylindrical body 1 typically made of glass and centered on an axis A and having at its front (right-hand in the drawing) end a bead forming an outwardly projecting ridge 1.1 and at its rear end another such bead 1.2. A plunger 2 projecting axially rearwardly from the body 1 carries inside this body 1 a piston 3 by means of which contents of the body 1 can be expelled from the front end. At its front end the body 1 carries a plug 4 having a flange or skirt 4.1 of cylindrical shape extending backward over the front end portion of the body 1 and fitting complementarily over the bead 1.1. A soft elastomeric seal disk or washer 7 is compressed axially between the plug 4 and the front end of the body 1. A finger crosspiece 6 is fixed to the rear end of the body 1 over the bead 1.2 like the plug 4. A needle 5 of conventional design passes through an axially throughgoing passage formed in the plug 4 and has a rear end fitting in a central hole 10 formed in the washer 7.

In FIG. 1 the plug 4, which is made of a fairly hard but still deformable synthetic resin, is formed with a radially outwardly projecting rim or collar 8 fitting complementarily in a protective cap or sleeve 9 into which the front end of the needle 5 is poked.

Figure 2:
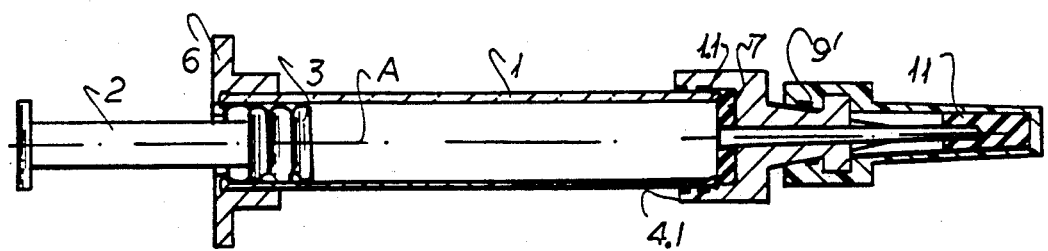

The arrangement of FIG. 2 is identical to that of FIG. 1 except that a cap 9' is formed of a very hard material and is provided internally with a sponge 11 into which the front end of the needle 5 is poked. Here as in FIG. 1 the rear end of the needle 5 is flush with the rear face of the washer 7.

Figure 3:
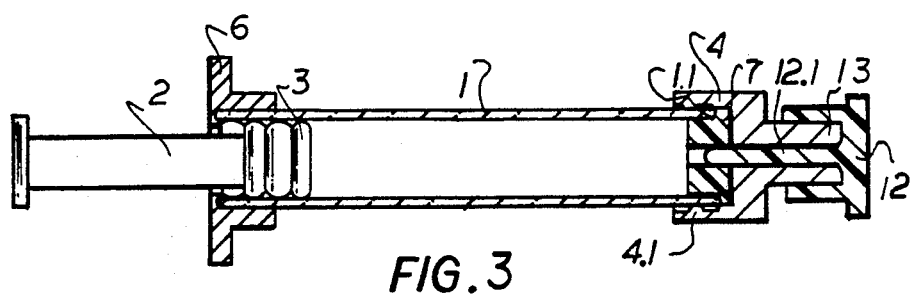

The system of FIG. 3 has no needle 5, but instead has a tip cap 12 fitting over a forwardly projecting end 13 of the plug 4 that has no rim 8. This tip cap has a rearwardly projecting pin 12.1 that extends along the axis A but that ends somewhat forward of the rear surface of the washer 7 which in this embodiment is axially considerably thicker than in FIGS. 1 and 2.

FIG. 4 shows an arrangement identical to that of FIG. 2, but with a washer 7 having no hole 10 and with a tip cap 12' having a pin 12.1' that ends at the front face of the washer 7. Thus to pierce the washer 7 it is necessary as shown in FIG. 5 to push the rear end of the needle 5 carried on a standard cup or collar 14 through it.

In FIG. 6 a mixing-type hypodermic is shown where the body 1 is subdivided by a partition piston 15 into a back compartment 16 adapted to hold a solvent and a front compartment holding a normally lyophilized medicament that can be dissolved by the solvent of the rear compartment 16. A bypass groove 18 is formed in the wall of the body 1 so that, when the piston 15 is level with it, fluid communication between the compartments 16 and 17 is possible in the manner well known in the art.

In this embodiment the skirt 4.1 of the plug 4 is formed with a pair of axially spaced radially inwardly open grooves 4.2 shaped to fit complementarily with the ridge 1.1 and between these grooves 4.2 with several radially throughgoing holes 19. These grooves 4.2 therefore define for the plug 4 a forward position shown in FIG. 6 and a rear position shown in FIG. 7. In the front FIG. 6 position the holes 19 are exposed so it is therefore possible to lyophilize a liquid in the front compartment 18 to form a dry medicament therein, while in the rear FIG. 7 position the syringe is hermetically closed.

The arrangement of FIG. 8 is identical to that of FIGS. 6 and 7 except that the plunger 2 has a threaded front portion 2.1 that prevents it from being simply depressed due to threaded engagement with the end piece cap 6. Thus to advance the piston 3 through the first half of its stroke the plunger 2 must be screwed in, ensuring gentle introduction of the contents of the rear compartment 16 into the front compartment 17. The rear portion of the plunger 2 is unthreaded and of relatively small diameter so that it can be depressed rapidly.

Finally, FIG. 9 shows an arrangement similar in function to that of FIG. 3, but with a cap 20 having a rear portion 20.1 permanently fixed to the plug 4 and a front portion 20.4 joined to this rear portion 20.1 by a weakened region 20.3 constituted by a groove in the wall of the cap 20. A pin 20.2 extends back from the front portion 20.4 like the pin 12.1 of the cap 12. The cap 20 is made of a hard but frangible material so that the front portion 20.4 can be broken at 20.3 from the rear portion 20.1. This makes the assembly tamperproof, by giving a clear and irreversible indication of any tampering.

I claim:

1. A hypodermic syringe comprising:
   a generally cylindrically tubular body extending along an axis and having an axial front end formed with a radially outwardly projecting annular bead, the body having a rear end provided with a finger-rest crosspiece;
   a piston axially displaceable in the body and provided with a plunger projecting axially out the rear end past the crosspiece, the crosspiece being internally threaded and the plunger having a complementarily externally threaded front portion threadedly engageable in the crosspiece and a small-diameter rear portion slidable axially through the crosspiece;
   a plug having a rearwardly directed flange fitting complementarily over the front end of the body at the bead and forwardly blocking the body; and
   a flat soft seal ring compressed axially between the plug and the front end of the body;

2. The syringe defined in claim 1, further comprising:
   a needle secured adhesively into the plug and having a rear end and a front end, the seal ring being formed with a central opening fitting around the rear needle end, the plug being formed with a radially outwardly projected securing rim; and
   a needle protector fitted over the needle and snugly engaged around the rim.

3. The syringe defined in claim 2 wherein the needle protector is made of a hard plastic and is provided with a soft seal body into which a front end of the needle is poked.

4. The syringe defined in claim 1 wherein the seal ring is formed with a central opening fitting snugly around the pin of the tip cap.

5. The syringe defined in claim 1 wherein the plug has a forwardly projecting collar adapted to fit with a separate needle assembly.

6. The syringe defined in claim 1, further comprising
   a partition plug axially slidable in the body between the piston and the front body end and forming in the body a rear compartment adapted to hold a solvent and a front compartment adapted to hold a dissolvable medicament, the body being formed generally centrally with an inwardly open bypass groove, the flange of the plug being formed with at least one radially throughgoing orifice, the plug being displaceable between a front position with the orifice forward of the body front end and thereby venting the front compartment and a rear position with the orifice backward of the body front end and blocked by the body.

7. A hypodermic syringe comprising:
   a generally cylindrically tubular body extending along an axis and having an axial front end formed with a radially outwardly projecting annular bead;

a piston axially displaceable in the body;

a plug having a rearwardly directed flange fitting complementarily over the front end of the body at the bead and forwardly blocking the body;

a flat soft seal ring compressed axially between the plug and the front end of the body; and a projective cap made of a hard but frangible material covering the plug and formed with a rear end fixed permanently to the plug, a front end fitting over and covering the plug, a pin projecting axially backward from the front end through the plug, and a weakened region joining the projective-cap front and rear ends.

8. The syringe defined in claim 7 wherein the body has a rear end provided with a finger-rest crosspiece and the piston is provided with a plunger projecting axially out the rear end past the crosspiece.

* * * * *